US011299743B2

(12) United States Patent
Kudithipudi et al.

(10) Patent No.: US 11,299,743 B2
(45) Date of Patent: Apr. 12, 2022

(54) GENETIC LOCUS IMPARTING A LOW ANATABINE TRAIT IN TOBACCO AND METHODS OF USING

(71) Applicant: ALTRIA CLIENT SERVICES LLC, Richmond, VA (US)

(72) Inventors: Chengalrayan Kudithipudi, Midlothian, VA (US); Alec J. Hayes, Chesterfield, VA (US); Robert Frank Hart, III, Midlothian, VA (US); Yanxin Shen, Glen Allen, VA (US); Jesse Frederick, Richmond, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 32 days.

(21) Appl. No.: 16/825,394

(22) Filed: Mar. 20, 2020

(65) Prior Publication Data

US 2020/0277617 A1    Sep. 3, 2020

Related U.S. Application Data

(63) Continuation of application No. 14/794,092, filed on Jul. 8, 2015, now Pat. No. 10,626,409.

(60) Provisional application No. 62/021,738, filed on Jul. 8, 2014.

(51) Int. Cl.
| | |
|---|---|
| *C12N 15/82* | (2006.01) |
| *A24B 13/00* | (2006.01) |
| *A01H 1/04* | (2006.01) |
| *A01H 6/82* | (2018.01) |
| *A01H 1/02* | (2006.01) |
| *A01H 1/06* | (2006.01) |
| *A01H 5/12* | (2018.01) |
| *C12Q 1/6895* | (2018.01) |

(52) U.S. Cl.
CPC ........... *C12N 15/8261* (2013.01); *A01H 1/02* (2013.01); *A01H 1/04* (2013.01); *A01H 1/06* (2013.01); *A01H 5/12* (2013.01); *A01H 6/823* (2018.05); *A24B 13/00* (2013.01); *C12N 15/8218* (2013.01); *C12N 15/8243* (2013.01); *C12Q 1/6895* (2013.01); *C12Q 2600/13* (2013.01); *C12Q 2600/156* (2013.01)

(58) Field of Classification Search
CPC .............................. A24B 13/00; C12N 15/8261
See application file for complete search history.

(56) References Cited

U.S. PATENT DOCUMENTS

| | | | |
|---|---|---|---|
| 4,516,590 A | 5/1985 | Teng | |
| 4,528,993 A | 7/1985 | Sensabaugh, Jr. et al. | |
| 4,660,577 A | 4/1987 | Sensabaugh et al. | |
| 4,683,195 A | 7/1987 | Mullis et al. | |
| 4,683,202 A | 7/1987 | Mullis et al. | |
| 4,761,373 A | 8/1988 | Anderson et al. | |
| 4,769,061 A | 9/1988 | Comai | |
| 4,800,159 A | 1/1989 | Mullis et al. | |
| 4,810,648 A | 3/1989 | Stalker | |
| 4,848,373 A | 7/1989 | Lenkey | |
| 4,940,835 A | 7/1990 | Shah et al. | |
| 4,965,188 A | 10/1990 | Mullis et al. | |
| 4,975,374 A | 12/1990 | Goodman et al. | |
| 5,013,659 A | 5/1991 | Bedbrook et al. | |
| 5,162,602 A | 11/1992 | Somers et al. | |
| 5,164,180 A | 11/1992 | Payne et al. | |
| 5,276,268 A | 1/1994 | Strauch et al. | |
| 5,372,149 A | 12/1994 | Roth et al. | |
| 5,545,565 A | 8/1996 | De Greve et al. | |
| 5,561,236 A | 10/1996 | Leemans et al. | |
| 5,767,366 A | 6/1998 | Sathasivan et al. | |
| 5,879,903 A | 3/1999 | Strauch et al. | |
| 5,928,937 A | 7/1999 | Kakefuda et al. | |
| 6,084,155 A | 7/2000 | Volrath et al. | |
| 6,166,302 A | 12/2000 | Merlo et al. | |
| 6,451,732 B1 | 9/2002 | Beckett et al. | |
| 6,451,735 B1 | 9/2002 | Ottaway et al. | |
| 7,293,564 B2 * | 11/2007 | Perfetti | A24B 3/12 131/290 |
| 2001/0016956 A1 | 8/2001 | Ward et al. | |
| 2004/0118422 A1 | 6/2004 | Lundin et al. | |
| 2005/0178398 A1 | 8/2005 | Breslin et al. | |
| 2005/0244521 A1 | 11/2005 | Strickland et al. | |
| 2006/0191548 A1 | 8/2006 | Strickland et al. | |
| 2007/0240728 A1 * | 10/2007 | Hashimoto | C12N 15/8218 131/280 |
| 2012/0024301 A1 | 2/2012 | Carroll et al. | |
| 2012/0031414 A1 | 2/2012 | Atchley et al. | |
| 2012/0031416 A1 | 2/2012 | Atchley et al. | |

(Continued)

FOREIGN PATENT DOCUMENTS

| | | |
|---|---|---|
| EP | 0 242 246 B1 | 11/1992 |
| EP | 2 537 929 A1 | 12/2012 |
| WO | WO 06/109197 A2 | 10/2006 |

OTHER PUBLICATIONS

Schiavinato, Matteo, et al. "Parental origin of the allotetraploid tobacco *Nicotiana benthamiana*." The Plant Journal 102.3 (2020): 541-554. (Year: 2020).*

(Continued)

*Primary Examiner* — Weihua Fan

(74) *Attorney, Agent, or Firm* — Arnold & Porter Kaye Scholer LLP; David R. Marsh; Yuhe Liu

(57) ABSTRACT

Provided herein are genetic markers and a coding sequence associated with a low- or ultra-low anatabine trait in tobacco.

18 Claims, 7 Drawing Sheets

Specification includes a Sequence Listing.

(56) References Cited

U.S. PATENT DOCUMENTS

| | | | |
|---|---|---|---|
| 2013/0056014 A1* | 3/2013 | Noguchi | C12N 15/8243 131/352 |
| 2015/0322451 A1* | 11/2015 | Kudithipudi | A24D 1/00 131/329 |

OTHER PUBLICATIONS

Sisson, Verne A., and R. F. Severson. "Alkaloid composition of the *Nicotiana* species." Beiträge zur Tabakforschung International 14.6 (1990): 327-339. (Year: 1990).*

Nekrasov, Vladimir, et al. "Targeted mutagenesis in the model plant *Nicotiana benthamiana* using Cas9 RNA-guided endonuclease." Nature biotechnology 31.8 (2013): 691-693 (Year: 2013).*

Chenna et al., "Multiple sequence alignment with the Clustal series of programs," *Nucleic Acids Research*, 31(13): 3497-3500 (2003).

DeBoer et al., "RNAi-mediated down-regulation of ornithine decarboxylase (ODC) leads to reduced nicotine and increased anatabine levels in transgenic *Nicotiana tabacum* L.," *Phytochemistry*, 72(4-5):344-355 (2011).

Dewey et al., "Molecular genetics of alkaloid biosynthesis in *Nicotiana tabacum*," *Phytochemistry*, 94:10-27 (2013).

Esakova et al., "Structure of Quinolinate Synthase from *Pyrococcus horikoshii* in the Presence of Its Product, Quinolinic Acid," *J. Am. Chem. Soc.*, 138(23):7224-7227 (2016).

Fischhoff et al., "Insect Tolerant Transgenic Tomato Plants," *Nature BioTechnology*, 5:807-813 (1987).

Hibi et al., "Gene Expression in Tobacco Low-Nicotine Mutants," Plant Cell. May 1994;6(5):723-35.

International Preliminary Report on Patentability dated Jan. 10, 2017, in International Application No. PCT/US2015/039562, 7 pgs.

International Search Report and Written Opinion dated Oct. 29, 2015, in International Application No. PCT/US2015/039562, 13 pgs.

Li et al., "Modularly assembled designer TAL effector nucleases for targeted gene knockout and gene replacement in eukaryotes," *Nucleic Acids Research*, 39(14): 6315-6325 (2011).

Nekrasov et al., "Targeted mutagenesis in the model plant *Nicotiana benthamiana* using Cas9 RNA-guided endonuclease," *Nature biotechnology*, 31(8):691-693 (2013).

Ollagnier-de Choudens et al., "Quinolinate synthetase, an iron-sulfur enzyme in NAD biosynthesis," *FEBS Letters*, 579:3737-3743 (2005).

Punta et al., "The Pfam protein families database," *Nucleic Acids Research*, 40:D290-D301 (2012).

Sun et al., "Genetic variation in alkaloid accumulation in leaves of *Nicotiana*," *J Zhejiang Univ Sci B.*, 14(12):1100-1109 (2013).

Sun et al., "An extended set of yeast-based functional assays accurately identifies human disease mutations," *Genome Research*, 26(5):670-680 (2016).

Timko, "Science Based Approaches for the Production and Evaluation of Modified Risk Tobacco Products," 96th Annual Tobacco Manufacturer's Association Conference Evidence-Based Science and Regulation of the Tobacco Industry Williamsburg VA, pp. 1-20 (2011) <http://www.tma.ore/tmalive/Html/Advertisements/Timko.pdf>.

Vaeck et al., "Transgenic plants protected from insect attack," *Nature*, 328:33-37 (1987).

Wang et al., "Silencing of PMT expression caused a surge of anatabine accumulation in tobacco," *Mol Biol Rep*, 36(8):2285-2289 (2009).

Weeks et al., "Use of designer nucleases for targeted gene and genome editing in plants," *Plant Biotechnol. J.*, 14:483-495 (2016).

Wei et al., "Testing computational prediction of missense mutation phenotypes: Functional characterization of 204 mutations of human cystathionine beta synthase," *Proteins: Structure, Function, and Bioinformatics*, 78(9):2058-2074 (2010).

Wright et al., "High-frequency homologous recombination in plants mediated by zinc-finger nucleases," *The Plant Journal*, 44:693-705 (2005).

Yoo et al., "*Arabidopsis* medophyll protoplasts: a versatile cell system for transient gene expression analysis," *Nature Protocols*, 2(7):1565-1572 (2007).

* cited by examiner

Panel A

Panel B

```
              1,448                            1,477
1. M207      AGGATGGGACA T  TATTGTTCATCCTCT
              D   G   T  [ ]  I   V   H   H   L

2. M544      AGGATGGGACATGTATTGTTCATCACCTCT
              D   G   T   C   I   V   H   H   L

3. Fc401 WT  AGGATGGGACATGTATTGTTCATCACCTCT
              D   G   T   C   I   V   H   H   L 1,536                      1,561
1. M207      CACACTTTGAAGTTCCTGGTGAAATG
              H   F   E   V   P   G   E   M

2. M544      CACACTTTGAA T  TCCTGGTGAAATG
              H   F   E  [ ]  P   G   E   M

3. Fc401 WT  CACACTTTGAAATTCCTGGTGAAATG
              H   F   E   V   P   G   E   M
```

Figure 4

```
 1. Fc401 WT      GTC IVHHL PGHEVVE NINE MY GDA FLTA HF EVPGE MF SLAM
 2. M207          GTY IVHHL PGHEVVE NINE MY GDA FLTA HF EVPGE MF SLAM
 3. M544          GTC IVHHL PGHEVVE NINE MY GDA FLTA HF EIPGE MF SLAM
 4. D5LAT9/169-49 GTC IVHHI FGGEVTE LVAA GY GDA YLAA HF EVPGE MF RLAM
 5. D5LAX9/215-54 GTC IVHHI FGGEVTE LVAA GY GDA YLAA HF EVPGE MF RLAM
 6. D7FHH3/111-39 GNC IVHHM PGDDVVE RVRS NHADA FHTA HL EVPGE MF RLAM
 7. D7MPK3/260-66 GTC IVHHL PGHEVVE RTKY MY CDA FITA HL EVPGE MF SLAM
 8. D7SHG8/133-45 GTC IVHHL PGHEVVE KTNE MY CDA FITA HL EVPGE MF SLAM
 9. D8QQE7/239-65 GSC IVHDM PGHDVVS RVRE GY GDA YLTA HF EVPGE MF TLAM
10. D8R818/237-56 GSC IVHDM PGHDVVS RVRE GY GDA YLTA HF EVPGE MF TLAM
11. D8U8Q3/237-49 GTC IVHHI FGGEVAE LVRR AY GDA YLAA HF EVPGE MF GLAM
```

Figure 5

GENETIC LOCUS IMPARTING A LOW ANATABINE TRAIT IN TOBACCO AND METHODS OF USING

CROSS-REFERENCE TO RELATED APPLICATIONS AND INCORPORATION OF SEQUENCE LISTING

This application is a continuation of U.S. patent application Ser. No. 14/794,092, filed Jul. 8, 2015, which claims the benefit of U.S. Provisional Application No. 62/021,738, filed Jul. 8, 2014, both of which are incorporated by reference in their entireties herein. A sequence listing contained in the file named "P34624US02_SL.TXT" which is 21,951 bytes (measured in MS-Windows®) and created on Mar. 20, 2020, is filed electronically herewith and incorporated by reference in its entirety.

TECHNICAL FIELD

This disclosure relates to genetic markers and the coding sequence associated with the locus that imparts a low anatabine trait in tobacco.

BACKGROUND

Anatabine is a minor alkaloid in tobacco and it is also a precursor for N'-nitrosoanatabine (NAT), one of four tobacco-specific nitrosamines (TSNAs) found in cured tobacco. Even though anatabine constitutes only about 3% of the total alkaloids found in tobacco, NAT constitutes about 40%-50% of the total amount of TSNAs. Therefore, reducing the amount of anatabine in a tobacco plant may be a viable way to reduce the overall amount of TSNAs in cured tobacco.

SUMMARY

This disclosure describes a correlation between a low anatabine trait and the quinolinate synthase (QS) gene. The correlation is useful for understanding the alkaloid synthesis pathway and its regulation, particularly with respect to anatabine. Single nucleotide polymorphisms (SNPs) in the QS gene also provide markers for breeding the low anatabine or ultra-low anatabine (ULA) trait into tobacco lines.

In one aspect, a tobacco hybrid, variety, line, or cultivar is provided that includes plants having a mutation in an endogenous nucleic acid having the sequence shown in SEQ ID NO: 7. In some embodiments, the mutant plants exhibit reduced expression or activity of QS. In some embodiments, leaf from the mutant plants exhibit reduced amounts of at least one alkaloid (e.g., anatabine). In some embodiments, cured leaf from the mutant plants exhibit a reduced amount of at least one TSNA (e.g., N'-nitrosoanatabine (NAT)).

In another aspect, seed produced by any of the tobacco hybrids, varieties, lines, or cultivars described herein, the seed including the mutation in an endogenous nucleic acid having the sequence shown in SEQ ID NO: 7.

In still another aspect, a method of making a tobacco plant is provided. Such a method typically includes the steps of inducing mutagenesis in Nicotiana tabacum cells to produce mutagenized cells; obtaining one or more plants from the mutagenized cells; and identifying at least one of the plants that comprises a mutation in an endogenous nucleic acid having the sequence shown in SEQ ID NO: 7.

In some embodiments, such a method further includes identifying at least one of the plants that comprises leaf exhibiting a reduced amount of at least one alkaloid relative to leaf from a plant lacking the mutation. In some embodiments, the at least one alkaloid is anatabine. In some embodiments, the method further includes identifying at least one of the plants that comprises leaf that, when cured, exhibit a reduced amount of at least one TSNA relative to cured leaf from a plant lacking the mutation. In some embodiments, the at least one TSNA is NAT.

In some embodiments, mutagenesis is induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. In some embodiments, mutagenesis is induced using TALEN. In some embodiments, mutagenesis is induced using zinc-finger technology.

In yet another aspect, a method for producing a tobacco plant is provided. Such a method typically includes the steps of: crossing at least one plant of a first tobacco line with at least one plant of a second tobacco line, the plant of the first tobacco line having a mutation in an endogenous nucleic acid having the sequence shown in SEQ ID NO: 7; and selecting for progeny tobacco plants that have the mutation.

In some embodiments, the method further includes selecting for progeny tobacco plants that comprise leaf exhibiting reduced expression or activity of QS relative to leaf from a plant lacking the mutation. In some embodiments, the method further includes selecting for progeny tobacco plants that comprise leaf exhibiting a reduced amount of at least one alkaloid relative to leaf from a plant lacking the mutation. In some embodiments, the at least one alkaloid is anatabine. In some embodiments, the method further includes selecting for progeny tobacco plants that comprise leaf that, when cured, exhibit a reduced amount of at least one TSNA relative to cured leaf from a plant lacking the mutation. In some embodiments, the at least one TSNA is NAT.

In still another aspect, a tobacco product is provided that includes cured leaf from a tobacco plant having a mutation in an endogenous nucleic acid having the sequence shown in SEQ ID NO: 7. In some embodiments, the leaf exhibits reduced expression or activity of QS relative to leaf from a plant lacking the mutation. In some embodiments, the leaf exhibits a reduced amount of at least one alkaloid relative to leaf from a plant lacking the mutation. A representative alkaloid is anatabine. In some embodiments, the cured leaf exhibits a reduced amount of at least one TSNA relative to cured leaf from a plant lacking the mutation. A representative TSNA is NAT.

In one aspect, a method of producing a tobacco product is provided. Such a method typically includes providing cured leaf from a tobacco plant having a mutation in an endogenous nucleic acid having the sequence shown in SEQ ID NO: 7; and manufacturing a tobacco product using the cured leaves. In some embodiments, the cured leaf exhibits reduced expression or activity of QS relative to cured leaf from a plant lacking the mutation. In some embodiments, the cured leaf exhibits a reduced amount of at least one alkaloid relative to cured leaf from a plant lacking the mutation. A representative alkaloid is anatabine. In some embodiments, the cured leaf exhibits a reduced amount of at least one TSNA relative to cured leaf from a plant lacking the mutation. A representative TSNA is NAT.

Any of the mutations described herein can include, without limitation, a point mutation, an insertion, a deletion, and a substitution.

In another aspect, a method of screening plants is provided. Such a method typically includes providing plant material from a plant as described herein; and determining the level of expression or activity of QS in the plant material. In still another aspect, a method of screening plants is provided. Such a method typically includes providing plant material from a plant as described herein; and determining the amount of at least one alkaloid in the plant material. In some embodiments, the at least one alkaloid is anatabine. In yet another aspect, a method of screening plants is provided. Such a method typically includes providing plant material from a plant as described herein; curing the plant material; and determining the amount of at least one TSNA in the plant material. In some embodiments, the at least one TSNA is NAT. In any of the methods described herein, the plant tissue can be leaf.

In another aspect, a method of identifying a tobacco plant or tobacco germplasm having a low or ultra-low anatabine phenotype is provided. Such a method typically includes detecting, in a tobacco plant or tobacco germplasm, at least one simple sequence repeat (SSR) of a marker locus that is associated with the phenotype, wherein the marker locus is represented by at least one of SEQ ID NOs: 1-6 or displays a recombination frequency of less than 10% with respect to a marker locus represented by at least one of SEQ ID NOs: 1-6 and maps to Linkage Group 6. In some embodiments, the detecting includes amplifying the marker locus or a portion of the marker locus with a primer pair and detecting the resulting amplicon. Representative primer pairs include, without limitation, SEQ ID NOs: 9 and 10, 11 and 12, 13 and 14, 15 and 16, 17 and 18, and 19 and 20.

In another aspect, a method of breeding is provided that includes crossing the tobacco plant or germplasm identified by a method described herein with a second tobacco plant or germplasm. In some embodiments, such a method further includes one or more steps of backcrossing, selfing, outcrossing, and selection of progeny plants. In some embodiments, such a method further includes the step of performing molecular marker analysis on DNA samples isolated from one or more progeny plants, wherein said analysis identifies a plant that includes at least one SSR selected from the group consisting of SEQ ID NOs: 1-6, wherein the SSR is associated with reduced amounts of anatabine in the progeny plants. In some embodiments, such a method further includes determining the amount of anatabine in leaf of the identified plant.

In yet another aspect, a method for detecting the presence of a marker linked to a gene associated with low or ultra-low anatabine in a tobacco plant is provided. Such a method typically includes analyzing chromosome 6 of the tobacco plant and detecting the presence of at least one SSR marker having a sequence selected from the group consisting of SEQ ID NOs: 1-5 and 6, and linked to a gene associated with low or ultra-low anatabine, wherein the presence of the at least one marker is indicative of a plant that exhibits low or ultra-low amounts of anatabine.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4 is an alignment of a portion of the QS sequence containing the mutations (SEQ ID NOs: 45-56 (top to bottom)).

FIG. 5 is an alignment of QS sequences (SEQ ID NOs: 34-44 (top to bottom)).

DETAILED DESCRIPTION

Figure 1:
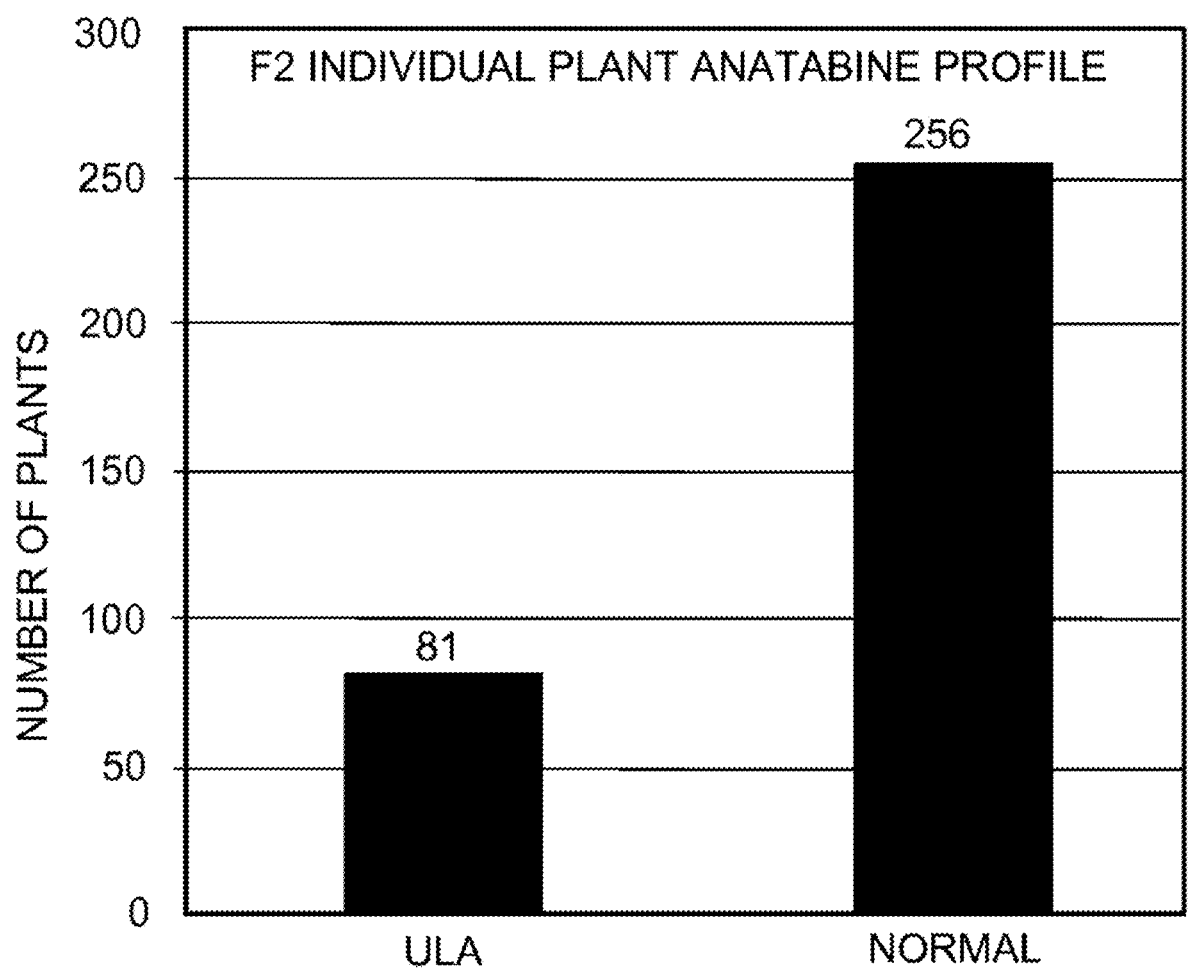
FIG. 1 is a graph showing the anatabine profiles of F2 individual plants.

Currently, there are no commercial tobacco varieties that exhibit reduced amounts of anatabine, and, prior to this disclosure, there were no known markers or genes associated with an ultra-low anatabine trait or even a low anatabine trait. As used herein, tobacco plants carrying an "ultra-low anatabine" trait (i.e., "ultra-low anatabine plants") are those plants having about 10% or less (e.g., about 9%, about 8%, about 7%, about 6%, about 5%, about 4%, about 3%, about 2%, about 1% or less (e.g., about 0%)) of the amount of anatabine that is typically present in a reference variety as shown in Table 1.

TABLE 1

| Reference Varieties | |
|---|---|
| Types | Reference Varieties |
| Burley | TN 90 LC, KT 204 LC, TN 86 LC, KDH959 |
| Dark | KY171, NL Madole, VA359, TR Madole |
| Flue | K326, K346, K394 |
| Oriental | Izmir, Basma Drama, Basma Zihna I, |
| Maryland | Maryland 609, Maryland 60, Maryland TI228 |
| Cigar | Caujaro, Florida 2612, Galpao |

A skilled artisan would appreciate that this corresponds to a reduction in the amount of anatabine, relative to a reference variety tobacco plant, by at least about 90% (e.g., at least about 91%, about 92%, about 93%, about 94%, about 95%, about 96%, about 97%, about 98%, about 99% or about 100% reduction)). As used herein, tobacco plants carrying a "low anatabine" trait (i.e., "low anatabine plants") are those plants having between about 50% and about 89% (e.g., between about 55% and about 85%, between about 60% and about 80%, between about 65% and about 75%, between about 50% and about 75%, between about 50% and about 60%, between about 60% and about 70%, or between about 70% and about 89%) of the amount of anatabine that is typically present in a reference variety tobacco plant. A skilled artisan would appreciate that this corresponds to a reduction in the amount of anatabine, relative to a reference variety tobacco plant, of between about 11% and about 50%

(e.g., between about 15% and about 45%, between about 20% and about 40%, between about 25% and about 35%, between about 15% and about 30%, between about 25% and about 45%, or between about 30% and about 50%).

As described herein, six simple sequence repeat (SSR) markers were identified that are tightly linked with the low anatabine trait in Nicotiana tabacum. The sequence of each of these markers is shown in SEQ ID NOs: 1-6. These markers can be used for breeding the low anatabine trait into varieties of interest. The genetic markers described herein also were used to identify the coding sequence associated with the locus. The gene was identified as quinolinate synthase (QS); the nucleic acid sequence of the cDNA is shown in SEQ ID NO: 7, while the encoded polypeptide is shown in SEQ ID NO: 8. Based on this discovery, the level of expression and/or the function of QS can be modulated in N. tabacum, thereby modulating the amount of TSNAs, particularly NAT, in cured tobacco and the resulting tobacco products.

Nucleic Acids and Polypeptides

A nucleic acid encoding wild type quinolinate synthase is provided herein (see, for example, SEQ ID NO: 7). As used herein, nucleic acids can include DNA and RNA, and includes nucleic acids that contain one or more nucleotide analogs or backbone modifications. A nucleic acid can be single stranded or double stranded, which usually depends upon its intended use. The wild type quinolinate synthase nucleic acid provided herein encodes a wild type quinolinate synthase polypeptide (see, for example, SEQ ID NO: 8).

Also provided are nucleic acids and polypeptides that differ from the wild type quinolinate synthase nucleic acid and polypeptide sequence (i.e., SEQ ID NO: 7 and 8, respectively). Nucleic acids and polypeptides that differ in sequence from SEQ ID NO: 7 and SEQ ID NO: 8 can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO: 7 and 8, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, 11, 13, 15, 17, 19, 21, 23, 25, 27, 29, 31, 33, 35, 37, 39, 41, 43, 45, 47, or 49), thereby leading to changes in the amino acid sequence of the encoded polypeptide (e.g., SEQ ID NOs: 2, 4, 6, 8, 10, 12, 14, 16, 18, 20, 22, 24, 26, 28, 30, 32, 34, 36, 38, 40, 42, 44, 46, 48, or 50). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain, and a "non-conservative amino acid substitution" is one in which an amino acid residue is replaced with an amino acid residue that does not have a similar side chain. See, for example, Dayhoff et al. (1978, in Atlas of Protein Sequence and Structure, 5(Suppl. 3):345-352), which provides frequency tables for amino acid substitutions.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny or potential progeny of such a cell. A host cell can be any prokaryotic or eukaryotic cell. For example, nucleic acids can be expressed in bacterial cells such as E. coli, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2xSSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Plants Having Reduced Amounts of NAT in Leaf and Methods of Making

Tobacco hybrids, varieties, lines, or cultivars are provided that have a mutation in an endogenous quinolinate synthase nucleic acid (e.g., SEQ ID NO: 7). The quinolinate synthase A protein (NadA) is a component of the quinolinate synthase complex, which includes quinolinate synthase A protein and L-aspartate oxidase protein. L-aspartate oxidase (NadB) is an FAD-dependent enzyme catalyzing the oxidation of L-aspartate to iminoaspartate. Iminoaspartate is then condensed with DHAP to form quinolinate under the action of quinolinate synthase A, the gene product of nadA.

As described herein, leaf from plants having a mutation in one or more of the endogenous nucleic acids (e.g., SEQ ID NO: 7) can exhibit a reduced amount of alkaloids (e.g., anatabine) and/or TSNAs (e.g., NAT) compared to leaf from a plant that lacks the mutation. In addition, leaf from plants having a mutation in an endogenous quinolinate synthase nucleic acid (e.g., SEQ ID NO: 7) can exhibit a reduced amount of alkaloids or TSNAs (e.g., compared to leaf from a plant lacking the mutation).

Methods of detecting one or more alkaloids and one or more TSNAs, and methods of determining the amount of one or more alkaloids and one or more TSNAs, are known in the art. For example, high performance liquid chromatography (HPLC)-mass spectroscopy (MS) (HPLC-MS) or high performance thin layer chromatography (HPTLC) can be used to detect the presence of and/or determine the amount of alkaloids or TSNAs. In addition, any number of chromatography methods (e.g., gas chromatography/thermal energy analysis (GC/TEA), liquid chromatography/mass spectrometry (LC/MS), and ion chromatography (IC)) can be used to detect the presence of and/or determine the amount of alkaloids or TSNAs.

Methods of making a tobacco plant having a mutation are known in the art. Mutations can be random mutations or targeted mutations. For random mutagenesis, cells (e.g., *Nicotiana tabacum* cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.*, 39(14):6315-25) or zinc-finger (see, for example, Wright et al., 2005, *The Plant J.*, 44:693-705). Whether random or targeted, a mutation can be a point mutation, an insertion, a deletion, a substitution, or combinations thereof.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss-of-function.

Preferably, a mutation in one of the novel nucleic acids disclosed herein results in reduced or even complete elimination of quinolinate synthase activity in a tobacco plant comprising the mutation. Suitable types of mutations in a quinolinate synthase coding sequence include, without limitation, insertions of nucleotides, deletions of nucleotides, or transitions or transversions in the wild-type quinolinate synthase coding sequence. Mutations in the coding sequence can result in insertions of one or more amino acids, deletions of one or more amino acids, and/or non-conservative amino acid substitutions in the encoded polypeptide. In some cases, the coding sequence comprises more than one mutation or more than one type of mutation.

Insertion or deletion of amino acids in a coding sequence, for example, can disrupt the conformation of the encoded polypeptide. Amino acid insertions or deletions also can disrupt sites important for recognition of the binding ligand (e.g., DHAP). It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the transporter polypeptide, introduce a stop codon to produce a truncated polypeptide, or disrupt an active site or domain (e.g., a catalytic site or domain, a binding site or domain) within the polypeptide.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, $M_0$ plants are regenerated from the mutagenized cells and those plants, or a subsequent generation of that population (e.g., $M_1$, $M_2$, $M_3$, etc.), can be screened for a mutation in a quinolinate synthase nucleic acid sequence (e.g., SEQ ID NO: 7). Screening for plants carrying a mutation in a sequence of interest can be performed using methods routine in the art (e.g., hybridization, amplification, combinations thereof) or by evaluating the phenotype (e.g., detecting and/or determining the amount of anatabine and/or NAT in the roots and/or the leaf). Generally, the presence of a mutation in a quinolinate synthase nucleic acid (e.g., SEQ ID NO: 7) results in a reduction of anatabine in the leaf of the mutant plants and NAT in the cured leaf of the mutant plants compared to a corresponding plant (e.g., having the same varietal background) lacking the mutation.

As used herein, "reduced" or "reduction" refers to a decrease (e.g., a statistically significant decrease) in the amount of anatabine in tobacco leaf, either green or cured, and/or NAT in cured leaf by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the mutation. As used herein, statistical significance refers to a p-value of less than 0.05, e.g., a p-value of less than 0.025 or a p-value of less than 0.01, using an appropriate measure of statistical significance, e.g., a one-tailed two sample t-test.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a quinolinate synthase nucleic acid sequence (e.g., SEQ ID NO: 7) can be selected. For example, plants in the $F_2$ or backcross generations can be screened using a marker developed from a sequence described herein or a fragment thereof, using one of the techniques listed herein. Leaf (green or cured, as appropriate) from progeny plants also can be screened for the amount of anatabine and/or NAT, and those plants having reduced amounts, compared to a corresponding plant that lacks the mutation, can be selected. Plants identified as possessing the mutant allele and/or the mutant phenotype can be back-crossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or chemical analyses of leaf (e.g., cured leaf) to determine the level of anatabine and/or NAT.

The result of a plant breeding program using the mutant tobacco plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

As used herein, the term "cultivar" refers to a uniform variety, strain or race of plant selected for desirable characteristics that are maintained by vegetative propagation or by inbred seed.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In addition to mutation, another way in which the amount of anatabine and NAT in tobacco leaf can be reduced is to use inhibitory RNAs (e.g., RNAi). Therefore, transgenic tobacco plants are provided that contain a transgene encoding at least one RNAi molecule, which, when transcribed, silences an endogenous quinolinate synthase nucleic acid (e.g., SEQ ID NO: 7). It would be understood in the art that "silencing" can refer to complete elimination or essentially complete elimination of the quinolinate synthase mRNA, resulting in 100% or essentially 100% reduction (e.g., greater than 95% reduction; e.g., greater than 96%, 97%, 98% or 99% reduction) in the amount of quinolinate synthase polypeptide; silencing also can refer to partial elimination of the quinolinate synthase mRNA (e.g., eliminating about 5%, 10%, 15%, 20%, 25%, 30%, 35%, 40%, 45%, 50% or more of the quinolinate synthase mRNA), resulting in a reduction (e.g., about 5%, 10%, 15%, 20%, 25%, 30%, 35%, 40%, 45%, 50% or more, but not complete elimination) in the amount of the quinolinate synthase polypeptide. As described herein, leaf from such transgenic plants exhibit a reduced amount of anatabine and NAT (e.g., compared to leaf from a plant lacking or not transcribing the RNAi).

RNAi technology is known in the art and is a very effective form of post-transcriptional gene silencing. RNAi molecules typically contain a nucleotide sequence (e.g., from about 18 to about 50 nucleotides in length) that is complementary to the target gene in both the sense and antisense orientations. The sense and antisense strands can be connected by a short "loop" sequence (e.g., about 5 to about 20 nucleotides in length) and transcribed in a single transcript, or the sense and antisense strands can be delivered to and transcribed in the target cells on separate vectors or constructs. A number of companies offer RNAi design and synthesis services (e.g., Life Technologies, Applied Biosystems).

The RNAi molecule can be transcribed using a plant expression vector. The RNAi molecule typically is at least 25 nucleotides in length and has at least 91% sequence identity (e.g., at least 95%, 96%, 97%, 98% or 99% sequence identity) to a quinolinate synthase nucleic acid sequence disclosed herein (e.g., SEQ ID NO: 7) or hybridizes under stringent conditions to a quinolinate synthase nucleic acid sequence disclosed herein (e.g., SEQ ID NO: 7). Hybridization under stringent conditions is described above.

Methods of introducing a nucleic acid (e.g., a heterologous nucleic acid) into plant cells are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation. Following transformation, the transgenic plant cells can be regenerated into transgenic tobacco plants. As described herein, transcription of the transgene results in leaf that exhibits a reduced amount of anatabine or NAT in the resulting cured leaf relative to leaf from a plant not transcribing the transgene. The leaves of the regenerated transgenic plants can be screened for the amount of anatabine or NAT in the resulting cured leaf, and plants having reduced amounts of anatabine or NAT in the resulting cured leaf, compared to the amount in a corresponding non-transgenic plant, can be selected for use in, for example, a breeding program as discussed herein.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order Lepidoptera. Exemplary genes include those that encode truncated CrylA(b) and CrylA(c) toxins. See, e.g., genes described in U.S. Pat. Nos. 5,545,565; 6,166,302; and 5,164,180. See also, Vaeck et al., 1997, Nature, 328:33-37 and Fischhoff et al., 1987, Nature Biotechnology, 5:807-813. Particularly useful are genes encoding toxins that exhibit insecticidal activity against Manduca sexta (tobacco hornworm); *Heliothis virescens* Fabricius (tobacco budworm) and/or *S. litura* Fabricius (tobacco cutworm).

Plants Having Increased Amounts of Anatabine in Leaf and Methods of Making

The sequences described herein can be overexpressed in plants in order to increase the amount of anatabine in the leaf. Therefore, transgenic tobacco plants, or leaf from such plants, are provided that include a plant expression vector. A plant expression vector typically includes a quinolinate synthase nucleic acid molecule described herein (e.g., SEQ ID NO: 7) or a functional fragment thereof under control of a promoter that is able to drive expression in plants (e.g., a plant promoter). As discussed herein, a nucleic acid molecule used in a plant expression vector can have a different sequence than a sequence described herein, which can be expressed as a percent sequence identity (e.g., relative to SEQ ID NO: 7) or based on the conditions under which the sequence hybridizes to SEQ ID NO: 7.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein, one of skill in the art can predict the portion(s) of a polypeptide (e.g., one or more domains) that may impart the desired functionality.

Following transformation, the transgenic tobacco cells can be regenerated into transgenic tobacco plants. The leaves of the regenerated tobacco plants can be screened for the amount of anatabine, and plants having increased amounts of anatabine, compared to the amount in a corresponding non-transgenic plant, can be selected and used, for example, in a breeding program as discussed herein. Expression of the nucleic acid molecule or a functional fragment thereof may result in leaf that exhibits an increased amount of anatabine compared to leaf from a tobacco plant that does not express the nucleic acid molecule or functional fragment thereof.

Genetic Markers of Low-/Ultra-Low-Anatabine Trait in Tobacco

Although coding sequences (i.e., the sequences that encode a protein) generally are well-conserved within a species, non-coding regions tend to accumulate polymorphism, and, therefore, can vary between individuals of the same species. Such regions provide the basis for genetic markers. In general, any differentially-inherited nucleic acid polymorphism that segregates among progeny is a potential genetic marker. The genomic variability that results in a genetic marker can be of any origin, including insertions, deletions, duplications, repetitive elements, point mutations, recombination events, and the presence and sequence of transposable elements.

In general, the identification of markers for MAS application involves determining the phenotype of the trait(s) of interest and genotyping the segregating population of progenies using polymorphic markers and genetic mapping of the desired trait. Details of mapping are described elsewhere herein. Polymorphic loci in the vicinity of the mapped trait are chosen as potential markers (typically, a marker locus closest to the locus of interest is a preferred marker). Linkage analysis is then used to determine which polymorphic marker allele sequence demonstrates a statistical likelihood of co-segregation with the desirable phenotype (thus, a "marker allele"). It is then possible to use this marker for rapid, accurate screening of plant lines for the marker allele without the need to grow the plants through their life cycle and await phenotypic evaluations.

Numerous methods for detecting genetic markers also are well-established. Markers corresponding to genetic polymorphisms between members of a population can be detected by numerous methods that are well-established in the art such as, without limitation, restriction fragment length polymorphisms, isozyme markers, allele specific hybridization (ASH), amplified variable sequences of the plant genome, self-sustained sequence replication, simple sequence repeats (SSRs), single nucleotide polymorphisms (SNPs), or amplified fragment length polymorphisms (AFLPs). The genetic markers described herein are SSRs. See, for example, any of SEQ ID NOs:1-6.

Genetic markers can facilitate mapping and selection of agriculturally important traits. A genetic marker that demonstrates linkage disequilibrium with a desired trait (e.g., low- or ultra-low-anatabine) can be a useful tool for marker-assisted selection (MAS), providing a means for rapid identification of desirable individuals or lines. Introgression of one or more particular genes into a cultivar or variety also can be facilitated by MAS. Simply by way of example, MAS can include the steps of (i) creating a map of genetic markers; (ii) determining statistical associations between one or more genetic markers and a phenotype (or phenotypic variability); (iii) identifying/defining a set of genetic markers associated with the phenotype (or phenotypic variability); and (iv) applying this information to a breeding program.

MAS can be used in plant breeding to assist in the efficient recovery of, for example, the recurrent parent genotype following backcrossing. In marker-assisted backcrossing, progeny can be selected for the donor trait (e.g., low- or ultra-low anatabine) and then repeatedly backcrossed to, for example, an elite line to reconstitute as much as possible of the elite line's background.

Tobacco Products and Methods of Making

The methods described herein allow for leaf constituents in a tobacco plant to be altered. As described herein, altering leaf constituents refers to reducing the amount of one or more alkaloids (e.g., anatabine) or one or more TSNAs (e.g., NAT) in the leaf or increasing the amount of one or more alkaloids (e.g., anatabine) in the leaf. As described herein, such methods can include mutagenesis (e.g., random or targeted) or the production of transgenic plants (using, e.g., RNAi or overexpression).

Leaf from such tobacco (e.g., having reduced amounts of one or more alkaloids or one or more TSNAs or increased amounts of one or more alkaloids) can be cured, aged, conditioned, and/or fermented. Methods of curing tobacco are well known and include, for example, air curing, fire curing, flue curing and sun curing. Aging also is known and typically is carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, smokeless tobacco products, tobacco-derived nicotine products (e.g., tobacco-derived nicotine pieces for use in the mouth), cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, cut tobacco, electronic cigarettes, electronic cigars, electronic cigarillos, and e-vapor devices. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the reduced-alkaloid tobacco, the reduced-TSNA tobacco, or the increased-alkaloid tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Mutagenesis

Since the biosynthetic pathway of anatabine and its associated genes is not completely known, a novel genetic variation was created in a population of tobacco plants to identify plants that have a significantly reduced ability to biosynthesize anatabine. These plants very likely have a mutated non-functional gene, critical for anatabine biosynthesis.

A population of the Flue-cured variety "401" was used in these experiments. Approximately 5000 seeds were treated with 0.6% ethyl methane sulfonate and germinated. M1 plants were grown in the field and M2 seeds were collected. Fifteen hundred M2 seeds were germinated and grown in 4-inch pots. At 50% flowering stage, plants were topped. Leaf samples were collected 2 weeks after topping and the samples screened for anatabine levels using high performance thin layer chromatography (HP-TLC) and gas chromatography.

After screening for alkaloids, two Flue Cured (FC) 401 ultra-low anatabine (ULA) lines were selected for trait development. It is noted that the amount of nicotine in both ULA lines is unchanged.

Example 2—Identification of Genetic Markers

To identify genetic marker(s) associated with the ULA trait, test crosses of FC401 mutant #1 (MS4144) were made with variety Red Russian and the F1s were selfed to generate F2 seed. Three hundred and thirty seven F2 plants were grown in the field and the alkaloids were analyzed individually. Depending on the anatabine levels, the mapping populations were grouped into ULA plants and normal plants (FIG. 1). Genomic DNA from each of the plants was extracted individually. To run simple sequence repeat (SSR) markers, DNA samples from 23 F2 ULA plants and 24 normal anatabine plants were pooled separately.

PCR reactions were performed in 25 µl final volumes which contained 25-50 ng of template DNA, 12.5 µl 2× Amplitaq PCR master mix ((Applied Biosystems [ABI]), 0.2 µM labeled primers (ABI), 1 µl 100% DMSO (Fisher Scientific), and 8 µl $H_2O$ (DNase/RNase free). Thermocycling conditions consisted of a 15 min incubation at 95° C.; followed by 34 cycles of 1 min at 94° C., 2 min at 60° C., 1 min at 72° C.; with a final reaction step of 60° C. for 30 min. All completed PCR reactions were diluted 1:50 with deionized water. Two microliters of diluted product was then combined with 9.75 µl HiDi Formamide (ABI) and 0.25 µl GeneScan 500 LIZ (ABI) size standard. Fragment analyses were performed. Samples were separated using a 36 cm capillary array in an ABI 3730 DNA Analyzer. Generated amplicons were analyzed using the "Local Southern Method" and the default analysis settings within GeneMapper v. 3.5 software (ABI). Final allele calls were standardized to an internal DNA control and based on the ABI 3730 DNA Analyzer.

Example 3—Linkage Mapping

A representative set of 246 SSR markers were selected and assessed in mapping parental lines (FC401×Red Russian). Of the 246 markers, 239 showed polymorphism among parents and were mapped and assessed for ULA trait screening. Six of those markers showed polymorphisms among ULA and non ULA traits and were tightly linked to the ULA trait. The six genetic markers are shown in Table 2, and all were found to be located on chromosome 6. Sequence information of the primer sets that were used are listed in Table 3.

TABLE 2

SSR markers tightly linked with ULA trait

| SSR Designation | SSR Sequence | SEQ ID NO |
|---|---|---|
| PT61163 | AGTGGCGGAGGTAGGAATTTCACCAAGAGAATTCAAA AAAATAAAAGTATACATGCAAAGAAGCAAACGTGATT CATCACCTAATATATATATATATATATATATATATAT ATATATATATATATATATATATATATATATATATACA TATACATAAAAATAAAATTTGACTTTATATACATAGT GTAATTTCCCGGCTACCTCACTCTTA | 1 |
| PT60043 | CCCTTTGCCACTTTACAAGAATTTTCCCTCATGTCGAG GGGATTCAACAGCTTTTATATATATATATATATATA AAGGAAAAAAGTAGTTGTTATCCTATTTGCACAA | 2 |
| PT60878 | AGCTCCATTTGTACTTCCGCGAGCGAGGTTCCAGACAG CCTATTTAATAATATATATATATATATATATATATT CACAAATATTGTGTATATACTACATACACACACATATA TAAAGTGTGCATAGTGTAAACAATAGCTCACTTATTCA CATAAGACTTAAGTTTGTATAATCATCTTGGAACGTCT GTTAGAA | 3 |
| PT61060 | CACAAGACCCTTCTTGGTGCTGTAGAAATTGAAAGAAAT GCAAAGGCTTTTTTTCTACTCTATCCTGTATTTCAATGT TTGGTGTGATTAAGCTATTATGCAGAATTTTGTATAGCA AGGAACCATATATATATATATATATATATATATATAT ATATACTAGACAGGGTTGCTGCCCAAAATATTAGGCGTG AAGCCTGTCTTGGTGGCAATATCAATAGTGCTCCGCCCA AAATATTAGGCGTGAAGCCTGTCTT | 4 |
| PT60925 | CAGAGATTACACCCATTGTGCTTCTTTTTAAAGGAGTAAA GTGGGAAAAAATCACCAAATACTTGAATAAAGACAGAGAA TAACCCCTCTCTCTCTCTCTCTCACACACACTCCTTTT TCGGCATTTATATTATAGAGCACACAGACAATAGATCTAT GGGTGAGAAAGATACTATTACTACCTACATTGACGGCGG | 5 |
| PT50801 | TGTCTCAACTTCTTGTCAATTGCTAATCACTCTTTTTATG GAATTGACATGCTACATATATATATATATATATATATA TTACTTTTCTTAGCAAATATATTTATAAGTATCGCAGGAT GACATAATAAGG | 6 |

TABLE 3

Primers used to detect the SSR markers

| Primer | Forward Primer | SEQ ID NO | Reverse Primer | SEQ ID NO |
|---|---|---|---|---|
| P161163 | AGTGGCGGAGGTAGGAATTT | 9 | TAAGAGTGAGGTAGCCGGGA | 10 |
| P160043 | CCCTTTGCCACTTTACAAGAA | 11 | TTGTGCAAATAGGATAACAACTACTTT | 12 |
| P160878 | AGCTCCATTTGTACTTCCGC | 13 | TTCTAACAGACGTTCCAAGATGA | 14 |
| P161060 | CACAAGACCCTTCTTGGTGC | 15 | ACGTGGAGTGGAGAAACCAG | 16 |
| P160925 | CAGAGATTACACCCATTGTGCT | 17 | CCGCCGTCAATGTAGGTAGT | 18 |
| P150801 | TGTCTCAACTTCTTGTCAATTGCT | 19 | CCTTATTATGTCATCCTGCGA | 20 |

Figure 2:
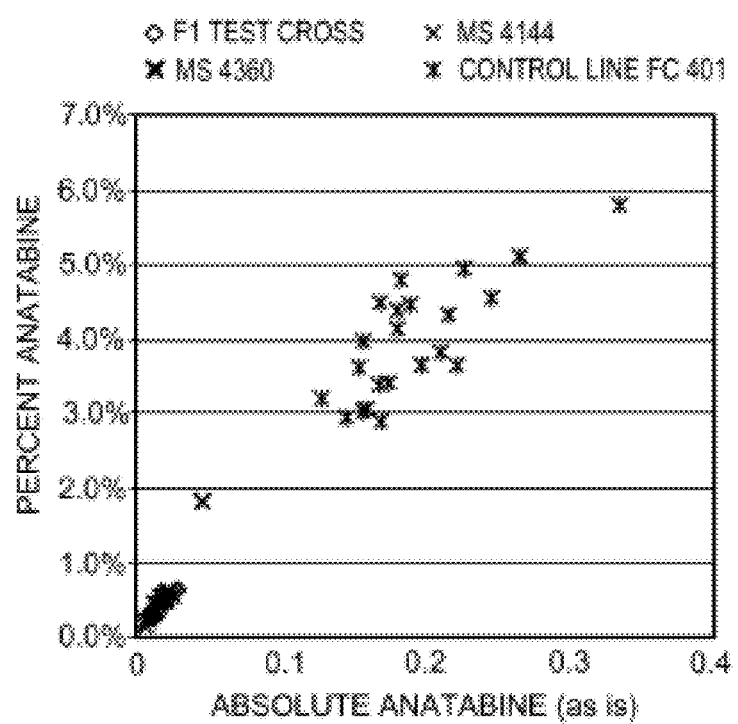
FIG. 2 depicts the results of experiments performed to examine the inheritance pattern of anatabine. Panel A shows the anatabine inheritance profile and Panel B is a graph showing the average percentage of anatabine for an F1 cross between the FC401 mutant #1 (MS4144)×FC401 Mutant #2 (MS4360).
Figure 2:
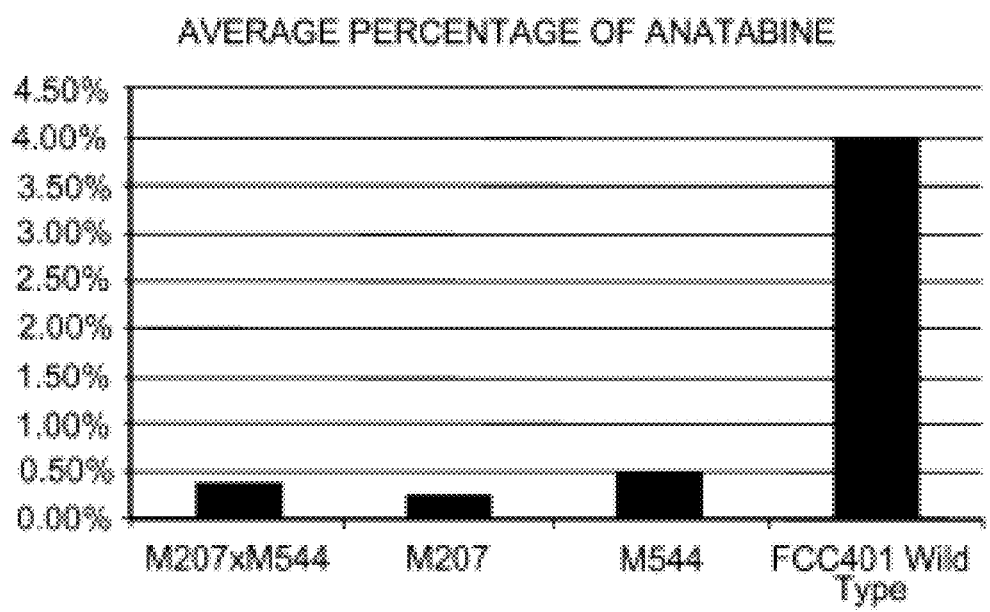

To evaluate the nature of the mutant gene in the FC401 ULA mutant #2, a cross between the FC401 mutant #1 and FC401 mutant #2 was made and the alkaloids were analyzed in the F1 generation. Even though they are two independent lines, the anatabine profile of F1 plants showed that they are mutants for the same gene (FIGS. 2A and 2B). Therefore, anatabine profile and genetic marker analysis indicate that a single recessive gene is critical for anatabine biosynthesis and is located on genetic linkage map 6.

Example 4—Identifying Candidate Genes

A list of candidate target genes that may be responsible for the low anatabine trait were generated from the following three different sets of gene expression data, as follows.

A) Methyl jasmonate up-regulated genes: Six samples of *Nicotiana tabacum* cultivar Bright Yellow—2, in two treatment groups of 3 samples each, are examined for gene expression. The first group consists of mock-treated control samples (CTR) obtained at 0, 48 and 72 hrs post-treatment. The second group consists of samples treated with methyl jasmonate and obtained at the same time points. Samples are analyzed by microarray (Cogenics), and log-ratio p-values and fold-changes for each probe are determined by Rosetta Resolver using the Agilent/Intensity-Pairwise Ratio Builder. These values are used to compare with the datasets from B) and C).

B) Topping up-regulated root expression genes: Forty eighty tobacco plants of the VA359 tobacco variety are grown in 10-inch pots. At 50% flowering, plants are topped; root samples are collected just before topping and at 30 mins, 2 hrs, 6 hrs, 12 hrs, 24 hrs, 72 hrs and 1 week post-topping. Six plants per time point are used for sample collection. Total RNA is isolated individually, equal amounts are pooled for each time point, and the samples hybridized with the tobacco microarray (Nimblegen). Log-ratio p-values and fold-changes for each array are determined by Rosetta Resolver using the Agilent/Intensity-Pairwise Ratio Builder. These values are used to compare with datasets from A) and C).

C) Methyl jasmonate up-regulated proteins: Triplicate samples of BY2 cells are mock-treated or treated with methyl jasmonate for 12, 24, and 48 hrs. Proteins from these samples are extracted and proteomic analysis is done by Biognosys Inc. Briefly, total proteins from the samples are used to produce a master list of all possible proteins that can be detected by the assay. Individual samples are then subjected to quantitative mass spectroscopy, and differential protein expression levels among each sample are generated. These values are used to compare gene expression profiles among the datasets from A) and B).

Example 5—Screening and Cloning Candidate Genes

Figure 3:
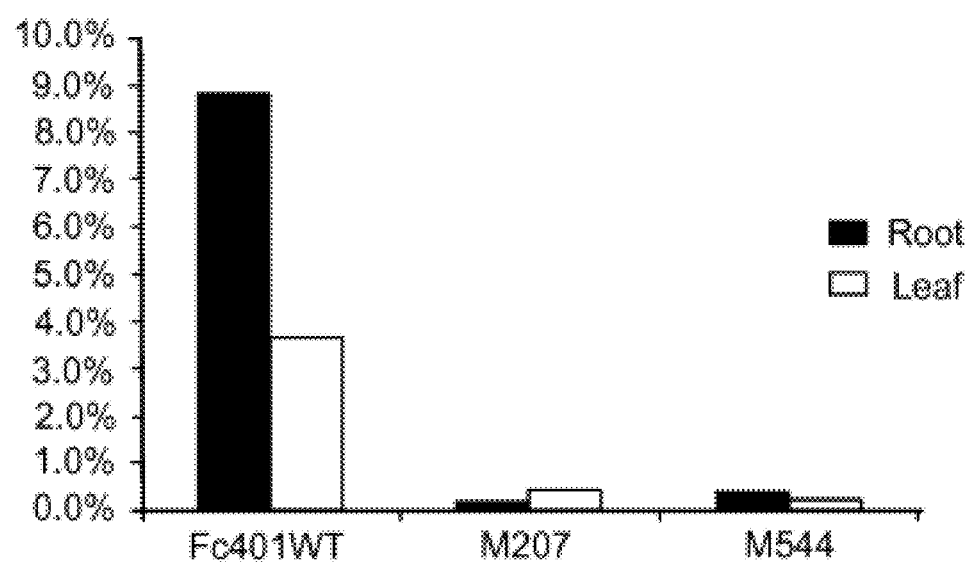
FIG. 3 is a graph showing the amount of anatabine in the root and leaf of reference variety tobacco plants and the two mutant tobacco plants.

Three tobacco lines, FC401 wild type (Wt); FC40-M207 mutant line fourth generation (M4) and FC401-M544 mutant line fourth generation (M4) were used for candidate gene screening. Low anatabine traits were confirmed for the two tobacco mutant lines (M207 and M544) in root and leaf before screening (see FIG. 3).

RNA was extracted from root tissues of wild type (Wt) FC401, M207 and M544 with RNeasy Plus Mini kit from Quiagen Inc. following the manufacturer's protocol. cDNA libraries were prepared from the RNAs using In-Fusion® SMARTer® Directional cDNA Library Construction Kit from Clontech Inc. cDNA libraries were diluted to 100 ng/µl and used as the template for candidate gene PCR screening.

PCR amplifications were performed in 50 µl final volumes that contained 50-100 ng of template DNA (i.e., the cDNA library) and 0.2 µM of primers (Fisher Scientific) using the Platinum® Taq DNA Polymerase High Fidelity kit (Life Technology Inc.). Thermocycling conditions included a 5 min incubation at 94° C.; followed by 34 cycles of 30 seconds at 94° C., 30 seconds at 58° C., 1 min 30 seconds at 68° C.; with a final reaction step of 68° C. for 7 mins. The PCR products were evaluated by agarose gel electrophoresis, and desired bands were gel purified and sequenced using an ABI 3730 DNA Analyzer (ABI).

51 candidate genes (listed in Table 4) were cloned from F401, Wt, M207 and M544 lines, and sequenced for single nucleotide polymorphism (SNP) detection.

TABLE 4

Listing of Candidate Genes for Screening

| | |
|---|---|
| Quinolinate Synthase A-1 | Pathogenesis related protein 1 |
| Allene oxide synthase | Allene oxide cyclase |

TABLE 4-continued

Listing of Candidate Genes for Screening

| | |
|---|---|
| ET861088.1 Methyl esterase | FH733463.1 TGACG-sequence specific transcription factor |
| FH129193.1 Aquaporin-Transport Universal stress protein Tabacum sequence | FH297656.1 Universal stress protein FH077657.1 Scarecrow-like protein |
| FH864888.1 EIN3-binding F-box protein | FH029529.1 4,5 DOPA dioxygenase |
| FI010668.1 Ethylene-responsive transcription factor | EB430189 Carboxylesterase |
| DW001704 Glutathione S transferase | EB683763 Bifunctional inhibitor/lipid transfer protein/seed storage 2 S albumin |
| DW002318 Serine/threonine protein kinase | DW004086 Superoxide dismutase |
| DW001733 Lipid transfer protein DIR1 | DW001944 Protein phosphatase 2 C |
| DW002033 | EB683763 Bifunctional inhibitor/lipid transfer protein/seed storage 2 S albumin |
| DW002318 Serine/threonine protein kinase | DW002576 Glycosyl hydrolase of unknown function DUF1680 |
| EB683279 | EB683763 |
| EB683951 | FG141784 (FAD Oxidoreductase) |
| BBLa-Tabacum sequences | BBLb |
| BBLc | BBLd |
| Pdr1 | Pdr2 |
| Pdr3 | Pdr5a |
| Pdr5b | NtMATE1 |
| NtMATE2 | NtMATE3 |
| WRKY8 | EIG-I24 |
| WRKY3 | WRKY9 |
| EIG-E17 | AJ748263.1 QPT2 quinolinate phosphoribosyltransferase |
| AJ748262.1 QPT1 | |

Example 6—SNP Detection and Characterization of the Mutants

Full length QS genes from the FC401 control and from the M207 and M544 mutant plants were cloned using AP23 and QSR1 primers which were designed using N. benthamiana QS gene sequence. The primer sequences are shown in Table 5. The cloned QS genes were sequenced and analyzed for mutations.

One SNP from M207 line and one SNP from M544 line were identified, and both SNPs were found to be located in the quinolinate synthase (QS) gene (FIG. 4).

In mutant line M544, the mutation is located 1546 nucleotides from the start codon. This G to A mutation results in an amino acid change from valine to isoleucine. In mutant line M207, the mutation is located 1460 nucleotides from the start codon. This G to A mutation results in an amino acid change from cysteine to tyrosine.

TABLE 5

Quinolinate Synthase Gene Screening Primers

| Name | Primer Sequence | SEQ ID NO |
|---|---|---|
| AP23 | ATCTTTGCTTCCTCGACTCCA | 21 |
| AP24 | AGTTAAGCGGAGCTTGATCGT | 22 |
| AP23Seq1 | ATGAGGTGCTGGCGTTGA | 23 |
| AP23Seq2 | TTCAGCGTAGCTGCCTTG | 24 |
| AP23Seq3 | GGAGTTTATCGGATGTCG | 25 |

TABLE 5-continued

Quinolinate Synthase Gene Screening Primers

| Name | Primer Sequence | SEQ ID NO |
|---|---|---|
| AP23Seq4 | TGTGCAGTAAGGAATGCATC | 26 |
| AP23Seq5 | GTTGTGAGCCGGTTCTGCAC | 27 |
| AP235pEND | ATGGACGCCGCAAATTTAGTCATGA | 28 |
| AP29F1 | AGTGACTCGGAAATAACTAAAGGGTTTT | 29 |
| AP29R1 | AAGTATTAGTCACAACATGCAGAGATGAG | 30 |
| AP29F2 | GAGCTCTTTCCATCTCTAGTAATCACA | 31 |
| AP29R2 | ATGTAGGTATCAGGACCATACAACACT | 32 |
| QSR1 | GTTCGAGGTAGAACCTACTAG | 33 |

Quinolinate Synthase A CDS-Fc401

(SEQ ID NO: 7)
ATGGATGCCGCAAATTTAGTCATGAAATCTTCCTTGTTTTCGAAATCCCC
ATGTCCCCTTTTTAGTTCTAAACTCATTCCTAGAGCACCACCCTCTGTCT
TTACTCTGCCTTCTACCTTTAGACCCCTCGTTAAATGCATACAAGCTTCA
TTCCCACCAAACCCTGATTCCAAAAAACCCTCAAACAATTCAACCTTTAC
GTGTTCAGCTGTGACTTCCTTCCCTTCTCAACAATCTCAGCCTCACGCGC
CTTCCGATGCCAAGCTCCAACTCCTGATCTCTGAATTCCAGTCCCTCGTC
GAACCAATGGACCGCGTGAAACGCCTCTTGCACTACTCCACACTCCTCCC
TCCAATGGACGCGTCCTTCAAAACCCCTGAGAATCGCGTACCGGGTTGCA
CTACACAGGTATGGCTGAACGTGAGTTTCGATGAGGCTGAGAACAGGATG
AAATTTTTGGCGGACAGTGACTCGGAAATAACTAAAGGGTTTTGCGCGTG
TTTGGTTTCGCTGCTGGACGGGGCTACTCCCGATGAGGTGCTGGCGTTGA
AAACGGAGGACTTGAATGCTTTGAATGTTGCGGGGTTGAACGGGAAAGGA
TCGGCATCTAGGGCGAATACGTGGCATAATGTGTTGGTCAGCATGCAGAA
AAGGACAAGGGCCTTAGTTGCGGAGCGTGAAGGCAGGCCGCGCGGCGAGC
TCTTTCCATCTCTAGTAATCACAGCTGATGGTATCCAACCCAAGGCAGC
TACGCTGAAGCCCAGGCAAGGTTCCTGTTTCCTGATGAATCAAGGGTCCA
AAAACTTGCCAATTTGCTAAAGGAGAAGAAAATAGGAGTTGTTGCTCATT
TCTACATGGACCCTGAGGTGCAAGGTGTTCTAACTGCAGCGCAGAAGCTT
TGGCCCCATATACATATATCTGATTCTTTAGTCATGGCTGATAAAGCTGT
CAGTATGGCAAAAGCTGGATGTGAATATATCTGTATTGGGTGTAGATT
TCATGTCAGAGAATGTGCGAGCCATTCTTGATCTAGCTGGATTCCCAGAG
GTTGGAGTTTATCGGATGTCGGACGAACGCATTGGTTGTTCTTTGGCTGA
TGCTGCAGCCAGCCCAGCATACTTGGATTATCTTAAAACAGCTTCAACTT
CTTCTCCATCTCTGCATGTTGTGTACATAAATACTTCACTGGAGACAAAA
GCATATTCTCATGAGCTTGTTCCGACTATAACATGTACTTCCTCTAATGT
TGTGCAAACTATTCTGCAGGCATTTGCTGAAGTACCTGACTTGGAAGTGT
TGTATGGTCCTGATACCTACATGGGTTCAAACATTGCGGAATTGTTCACC

CAGATGTCCACGATGACTGATGAAGAAATTTCTGCGATACATCCTTTGCA
CAACAGAATCTCCATTAAATCTTTGCTTCCTCGACTGCATTATTTTCAGG
ATGGGACATGTATTGTTCATCACCTCTTTGGTCATGAAGTTGTGGAGAAG
ATAAATGAAATGTATGGGGATGCATTCCTTACTGCACACTTTGAAGTTCC
TGGTGAAATGTTTTCCCTGGCAATGGAAGCGAAGAAAAGGGGCATGGGAG
TAGTAGGTTCTACCTCGAACATACTCGACTTTATCAAAGAAAGGGTAGAA
GAGTCCTTGAATAGAAACGTAGATGAACATCTTCAGTTTGTTTTGGGAAC
GGAATCAGGAATGATTACGGCAATAGTTGCAGCAGTCGGTAAATTACTAG
GTTCTGCTGACTCCTCTTCCGGTGGAGCAAAAGTAAGTGTTGAGATTGTC
TTTCCTGTCTCGTCAGAATCAGTGACAAGAACATCTACGGGTTCGCCTCT
GGACCAAAATAAGGTCAATATTATACCTGGAGTTGCAAGTGGAGAGGGGT
GTTCTCTACATGGTGGATGTGCCTCCTGTCCATATATGAAGATGAACTCT
CTTAGCTCGTTGCTAAAAGTTTGCCAGAGCTTGCCCCATGGCAAAGCCGA
ACTTTCAGCTTATGAGGCAGGACGATTCAGTTTGCGAACCCCCAAGGGAA
AACAAATTGCGGATGTTGGTTGTGAGCCGGTTCTGCACATGAGACACTTT
CAGGCAACAAAGAGATTACCAGAGCAGCTAATCAATCAAATACTTCAACG
ATCAAGCTCTGCTTAA (SEQ ID NO: 8)
MDAANLVMKSSLFSKSPCPLFSSKLIPRAPPSVFTLPSTFRPLVKCIQAS
FPPNPDSKKPSNNSTFTCSAVTSFPSQQSQPHAPSDAKLQLLISEFQSLV
EPMDRVKRLLHYSTLLPPMDASFKTPENRVPGCTTQVWLNVSFDEAENRM
KFLADSDSEITKGFCACLVSLLDGATPDEVLALKTEDLNALNVAGLNGKG
SASRANTWHNVLVSMQKRTRALVAEREGRPRGELFPSLVITADGIQPQGS
YAEAQARFLFPDESRVQKLANLLKEKKIGVVAHFYMDPEVQGVLTAAQKL
WPHIHISDSLVMADKAVSMAKAGCEYISVLGVDFMSENVRAILDLAGFPE
VGVYRMSDERIGCSLADAAASPAYLDYLKTASTSSPSLHVVYINTSLETK
AYSHELVPTITCTSSNVVQTILQAFAEVPDLEVLYGPDTYMGSNIAELFT
QMSTMTDEEISAIHPLHNRISIKSLLPRLHYFQDGTCIVHHLFGHEVVEK
INEMYGDAFLTAHFEVPGEMFSLAMEAKKRGMGVVGSTSNILDFIKERVE
ESLNRNVDEHLQFVLGTESGMITAIVAAVGKLLGSADSSSGGAKVSVEIV
FPVSSESVTRTSTGSPLDQNKVNIIPGVASGEGCSLHGGCASCPYMKMNS
LSSLLKVCQSLPHGKAELSAYEAGRFSLRTPKGKQIADVGCEPVLHMRHF
QATKRLPEQLINQILQRSSSA

There are 2787 QS genes listed in Pfam protein data base and 41 of the QS genes are from plants (The Pfam protein family database; Punta et al., Nuc. Acids Res., 2012, 40:D290-D301). The alignment that is shown in FIG. 5 compares the amino acid sequences of the wild type QS and the two mutant lines with respect to representative plant QS sequences. The M207 mutation (C to Y) is conserved in all but one of the 2787 QS sequences deposited in the Pfam database. The M544 mutation (V to I) is conserved only in plants and not in other QS genes.

To confirm the stability of the mutations, the QS gene was sequenced in multiple generations of mutants. The QS gene mutation patterns correlated with the anatabine levels of the mutant lines, indicating that the QS gene mutation is responsible for the ultra-low anatabine trait. See Table 6.

TABLE 6

Stability of mutant lines

| Line ID | M2 Seed | M3 Seed | M4 Seed | SNP |
|---|---|---|---|---|
| M207 | MS103 Heterozygous | MS4144 Homozygous | MS13379 Homozygous | Homozygous |
|  |  |  | MS13396 Homozygous | Homozygous |
|  |  |  | MS13397 Homozygous | Homozygous |
|  |  |  | MS13398 Homozygous | Homozygous |
|  |  |  | MS13399 Homozygous | Homozygous |
|  |  |  | MS13400 Heterozygous | Heterozygous |
|  |  |  | MS13401 Homozygous | Homozygous |
|  |  |  | MS13473 Homozygous | Homozygous |
|  |  |  | MS13537 Homozygous | Homozygous |
|  |  |  | MS13374 Homozygous | Homozygous |
|  |  | MS12469 Heterozygous | MS13391 Homozygous | Homozygous |
|  |  |  | MS13392 Homozygous | Homozygous |
|  |  |  | MS13393 Homozygous | Homozygous |
| M544 | MS445 Heterozygous | M54360 Homozygous | MS13474 Homozygous | Homozygous |
|  |  |  | MS13540 Homozygous | Homozygous |
|  |  | MS12471 Heterozygous | MS13370 Homozygous | Homozygous |
|  |  |  | MS13371 Homozygous | Homozygous |
|  |  |  | MS13389 Homozygous | Homozygous |

Figure 6:
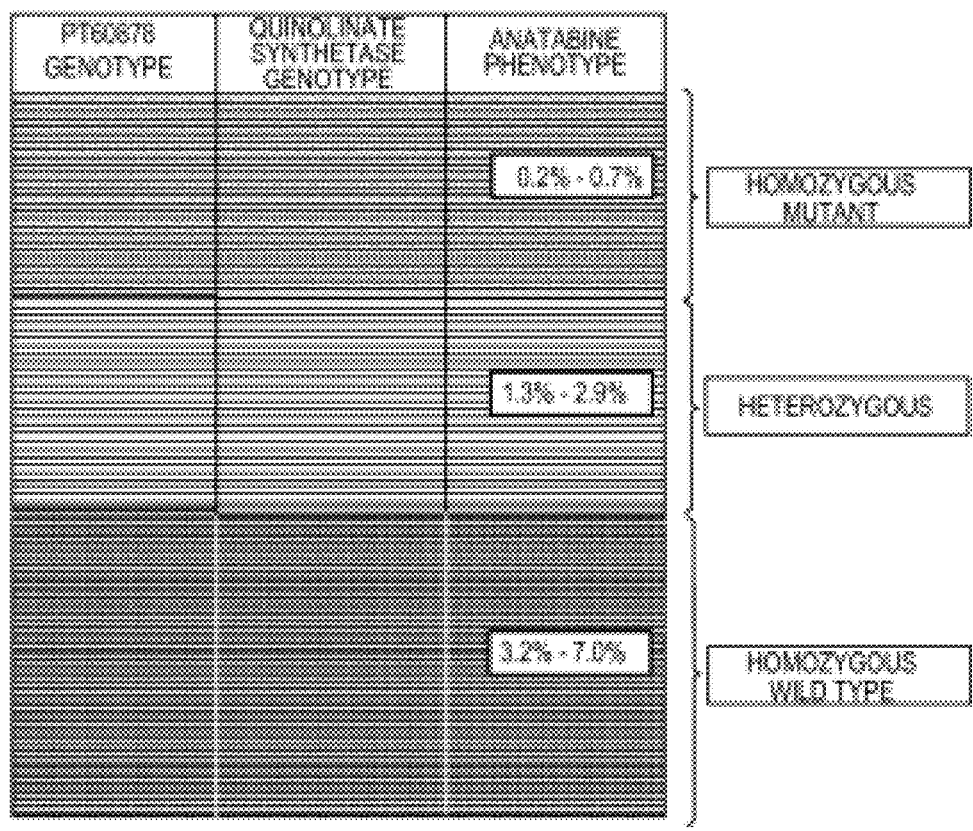
FIG. 6 is an image showing co-segregation of the mutants with anatabine.

Example 7—Confirmation of Linkage Between the Quinolinate Synthase Gene and the Ultra-Low Anatabine Phenotype In order to verify the linkage between the low anatabine phenotype and the QS SNP genotype, a mapping population was tested for both anatabine level and SNPs. The mapping population was generated previously by crossing mutant line M207 and wild type Red Russian. FIG. 6 shows the linkage between the anatabine trait, the PT60808 genetic marker, which is the genetic marker that is the most tightly linked to the trait, and the QS mutation. From 115 F2 plants tested, the QS mutation co-segregated with the low anatabine trait.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A tobacco plant having an induced mutation in an endogenous gene, wherein the endogenous gene has a sequence 100% identical to SEQ ID NO: 7.

2. The tobacco plant of claim 1, wherein the mutant plant exhibits reduced expression or activity of quinolinate synthase as compared to a control plant lacking the induced mutation.

3. The tobacco plant of claim 1, wherein leaf from the mutant plant comprises a reduced amount of at least one alkaloid as compared to leaf from a control plant lacking the induced mutation.

4. The tobacco plant of claim 3, wherein the alkaloid is anatabine.

5. The tobacco plant of claim 1, wherein cured leaf from the mutant plant exhibits a reduced amount of at least one tobacco-specific nitrosamine (TSNA) as compared to cured leaf from a control tobacco plant lacking the induced mutation.

6. The tobacco plant of claim 5, wherein the at least one TSNA is N'-nitrosoanatabine (NAT).

7. Seed produced by the tobacco plant of claim 1, wherein the seed comprises the induced mutation.

8. The tobacco plant of claim 1, wherein the induced mutation provides an amino acid substitution at a position corresponding to the cysteine residue at position 487 or the valine residue at position 516 of SEQ ID NO: 8.

9. The tobacco plant of claim 1, wherein the induced mutation comprises a tyrosine at amino acid position 487 of SEQ ID NO: 8.

10. The tobacco plant of claim 1, wherein the induced mutation comprises an isoleucine at position 516 of SEQ ID NO: 8.

11. The tobacco plant of claim 4, wherein the reduced amount of anatabine comprises a reduction of about 50% to about 95% as compared to a control plant lacking the induced mutation.

12. The tobacco plant of claim 1, wherein cured leaf from the tobacco plant comprises an anatabine percentage of less than 0.5%.

13. The tobacco plant of claim 1, wherein the induced mutation is in a residue fully conserved in the wild-type quinolinate synthase proteins.

14. A method for producing a tobacco seed comprising:
(a) crossing a first tobacco plant having an induced mutation in an endogenous gene, wherein the endogenous gene has a sequence 100% identical to SEQ ID NO: 7 with a second tobacco plant to produce at least one progeny seed; and
(b) selecting at least one progeny seed from step (a) that comprises said induced mutation.

15. The method of claim 14, wherein the first tobacco plant exhibits reduced expression or activity of quinolinate synthase as compared to a control plant lacking the induced mutation.

16. The method of claim 14, wherein the induced mutation provides an amino acid substitution at a position corresponding to the cysteine residue at position 487 or the valine residue at position 516 of SEQ ID NO: 8.

17. A method of making a tobacco plant comprising:
(a) inducing mutagenesis in a Nicotiana tabacum cell to produce a mutagenized cell;
(b) obtaining one or more plants regenerated from the mutagenized cell of step (a); and
(c) identifying at least one plant from step (b) that comprises an induced mutation in an endogenous gene, wherein the endogenous gene has a sequence 100% identical to SEQ ID NO: 7.

18. The method of claim 17, wherein the at least one plant identified in step (c) exhibits reduced expression or activity of quinolinate synthase as compared to a control plant lacking the induced mutation.

* * * * *

SEQUENCE LISTING

<160> NUMBER OF SEQ ID NOS: 56

<210> SEQ ID NO 1
<211> LENGTH: 211
<212> TYPE: DNA
<213> ORGANISM: Nicotiana tabacum

<400> SEQUENCE: 1

```
agtggcggag gtaggaattt caccaagaga attcaaaaaa ataaaagtat acatgcaaag      60
aagcaaacgt gattcatcac ctaatatata tatatatata tatatatata tatatatata     120
tatatatata tatatatata tatatacata tacataaaaa taaaatttga ctttatatac     180
atagtgtaat ttcccggcta cctcactctt a                                    211
```

<210> SEQ ID NO 2
<211> LENGTH: 110
<212> TYPE: DNA
<213> ORGANISM: Nicotiana tabacum

<400> SEQUENCE: 2

```
ccctttgcca ctttacaaga attttccctc atgtcgaggg gattcaacag cttttatata      60
tatatatata tatataaagg aaaaaagtag ttgttatcct atttgcacaa                 110
```

<210> SEQ ID NO 3
<211> LENGTH: 197
<212> TYPE: DNA
<213> ORGANISM: Nicotiana tabacum

<400> SEQUENCE: 3

```
agctccattt gtacttccgc gagcgaggtt ccagacagcc tatttaataa tatatatata      60
tatatatata tatattcaca aatattgtgt atatactaca tacacacaca tatataaagt     120
gtgcatagtg taaacaatag ctcacttatt cacataagac ttaagtttgt ataatcatct     180
tggaacgtct gttagaa                                                   197

<210> SEQ ID NO 4
<211> LENGTH: 259
<212> TYPE: DNA
<213> ORGANISM: Nicotiana tabacum

<400> SEQUENCE: 4
cacaagaccc ttcttggtgc tgtagaaatt gaaagaaatg caaaggcttt ttttctactc      60
tatcctgtat ttcaatgttt ggtgtgatta agctattatg cagaattttg tatagcaagg     120
aaccatatat atatatatat atatatatat atatatatat actagacagg gttgctgccc     180
aaaatattag gcgtgaagcc tgtcttggtg gcaatatcaa tagtgctccg cccaaaatat     240
taggcgtgaa gcctgtctt                                                 259

<210> SEQ ID NO 5
<211> LENGTH: 199
<212> TYPE: DNA
<213> ORGANISM: Nicotiana tabacum

<400> SEQUENCE: 5
cagagattac acccattgtg cttcttttta aaggagtaaa gtgggaaaaa atcaccaaat      60
acttgaataa agacagagaa taacccctct ctctctctct ctctcacaca cactcctttt     120
tcggcattta tattatagag cacacagaca atagatctat gggtgagaaa gatactatta     180
ctacctacat tgacggcgg                                                 199

<210> SEQ ID NO 6
<211> LENGTH: 132
<212> TYPE: DNA
<213> ORGANISM: Nicotiana tabacum

<400> SEQUENCE: 6
tgtctcaact tcttgtcaat tgctaatcac tcttttatg gaattgacat gctacatata       60
tatatatata tatatatata ttactttct tagcaaatat atttataagt atcgcaggat      120
gacataataa gg                                                        132

<210> SEQ ID NO 7
<211> LENGTH: 2166
<212> TYPE: DNA
<213> ORGANISM: Nicotiana tabacum

<400> SEQUENCE: 7
atggatgccg caaatttagt catgaaatct tccttgtttt cgaaatcccc atgtcccctt      60
tttagttcta aactcattcc tagagcacca ccctctgtct ttactctgcc ttctaccttt     120 agaccctcg ttaaatgcat acaagcttca ttcccaccaa accctgattc caaaaaaccc     180
tcaaacaatt caacctttac gtgttcagct gtgacttcct tcccttctca acaatctcag    240
cctcacgcgc cttccgatgc caagctccaa ctcctgatct ctgaattcca gtccctcgtc    300
gaaccaatgg accgcgtgaa acgcctcttg cactactcca cactcctccc tccaatggac    360
gcgtccttca aaaccctga gaatcgcgta ccggttgca ctacacaggt atggctgaac      420
gtgagtttcg atgaggctga gaacaggatg aaattttggg cggacagtga ctcggaaata    480
```

-continued

```
actaaagggt tttgcgcgtg tttggtttcg ctgctggacg gggctactcc cgatgaggtg      540
ctggcgttga aaacggagga cttgaatgct ttgaatgttg cggggttgaa cgggaaagga      600
tcggcatcta gggcgaatac gtggcataat gtgttggtca gcatgcagaa aaggacaagg      660
gccttagttg cggagcgtga aggcaggccg cgcggcgagc tctttccatc tctagtaatc      720
acagctgatg gtatccaacc ccaaggcagc tacgctgaag cccaggcaag gttcctgttt      780
cctgatgaat caagggtcca aaaacttgcc aatttgctaa aggagaagaa aataggagtt      840
gttgctcatt tctacatgga ccctgaggtg caaggtgttc taactgcagc gcagaagctt      900
tggccccata tacatatatc tgattcttta gtcatggctg ataaagctgt cagtatggca      960
aaagctggat gtgaatatat atctgtattg ggtgtagatt tcatgtcaga gaatgtgcga     1020
gccattcttg atctagctgg attcccagag gttggagttt atcggatgtc ggacgaacgc     1080
attggttgtt ctttggctga tgctgcagcc agcccagcat acttggatta tcttaaaaca     1140
gcttcaactt cttctccatc tctgcatgtt gtgtacataa atacttcact ggagacaaaa     1200
gcatattctc atgagcttgt tccgactata acatgtactt cctctaatgt tgtgcaaact     1260
attctgcagg catttgctga agtacctgac ttggaagtgt tgtatggtcc tgatacctac     1320
atgggttcaa acattgcgga attgttcacc cagatgtcca cgatgactga tgaagaaatt     1380
tctgcgatac atcctttgca aacagaatc tccattaaat ctttgcttcc tcgactgcat     1440
tattttcagg atgggacatg tattgttcat cacctctttg gtcatgaagt tgtggagaag     1500
ataaatgaaa tgtatgggga tgcattcctt actgcacact tgaagttcc tggtgaaatg     1560 ttttccctgg caatggaagc gaagaaaagg ggcatgggag tagtaggttc tacctcgaac     1620
atactcgact ttatcaaaga aagggtagaa gagtccttga atagaaacgt agatgaacat     1680
cttcagtttg ttttgggaac ggaatcagga atgattacgg caatagttgc agcagtcggt     1740
aaattactag gttctgctga ctcctcttcc ggtggagcaa aagtaagtgt tgagattgtc     1800
tttcctgtct cgtcagaatc agtgacaaga acatctacgg gttcgcctct ggaccaaaat     1860
aaggtcaata ttatacctgg agttgcaagt ggagaggggt gttctctaca tggtggatgt     1920
gcctcctgtc catatatgaa gatgaactct cttagctcgt tgctaaaagt ttgccagagc     1980
ttgccccatg gcaaagccga actttcagct tatgaggcag gacgattcag tttgcgaacc     2040
cccaagggaa aacaaattgc ggatgttggt tgtgagccgg ttctgcacat gagacacttt     2100
caggcaacaa agagattacc agagcagcta atcaatcaaa tacttcaacg atcaagctct     2160
gcttaa                                                                2166
```

<210> SEQ ID NO 8
<211> LENGTH: 721
<212> TYPE: PRT
<213> ORGANISM: Nicotiana tabacum

<400> SEQUENCE: 8

```
Met Asp Ala Ala Asn Leu Val Met Lys Ser Ser Leu Phe Ser Lys Ser
1               5                   10                  15

Pro Cys Pro Leu Phe Ser Ser Lys Leu Ile Pro Arg Ala Pro Pro Ser
            20                  25                  30

Val Phe Thr Leu Pro Ser Thr Phe Arg Pro Leu Val Lys Cys Ile Gln
        35                  40                  45

Ala Ser Phe Pro Pro Asn Pro Asp Ser Lys Lys Pro Ser Asn Asn Ser
    50                  55                  60
```

-continued

```
Thr Phe Thr Cys Ser Ala Val Thr Ser Phe Pro Ser Gln Gln Ser Gln
 65                  70                  75                  80

Pro His Ala Pro Ser Asp Ala Lys Leu Gln Leu Leu Ile Ser Glu Phe
                 85                  90                  95

Gln Ser Leu Val Glu Pro Met Asp Arg Val Lys Arg Leu Leu His Tyr
            100                 105                 110

Ser Thr Leu Leu Pro Pro Met Asp Ala Ser Phe Lys Thr Pro Glu Asn
            115                 120                 125

Arg Val Pro Gly Cys Thr Thr Gln Val Trp Leu Asn Val Ser Phe Asp
            130                 135                 140

Glu Ala Glu Asn Arg Met Lys Phe Leu Ala Asp Ser Asp Ser Glu Ile
145                 150                 155                 160

Thr Lys Gly Phe Cys Ala Cys Leu Val Ser Leu Leu Asp Gly Ala Thr
                165                 170                 175

Pro Asp Glu Val Leu Ala Leu Lys Thr Glu Asp Leu Asn Ala Leu Asn
            180                 185                 190

Val Ala Gly Leu Asn Gly Lys Gly Ser Ala Ser Arg Ala Asn Thr Trp
            195                 200                 205

His Asn Val Leu Val Ser Met Gln Lys Arg Thr Arg Ala Leu Val Ala
210                 215                 220

Glu Arg Glu Gly Arg Pro Arg Gly Glu Leu Phe Pro Ser Leu Val Ile
225                 230                 235                 240

Thr Ala Asp Gly Ile Gln Pro Gln Gly Ser Tyr Ala Glu Ala Gln Ala
                245                 250                 255

Arg Phe Leu Phe Pro Asp Glu Ser Arg Val Gln Lys Leu Ala Asn Leu
            260                 265                 270

Leu Lys Glu Lys Lys Ile Gly Val Val Ala His Phe Tyr Met Asp Pro
            275                 280                 285

Glu Val Gln Gly Val Leu Thr Ala Ala Gln Lys Leu Trp Pro His Ile
            290                 295                 300

His Ile Ser Asp Ser Leu Val Met Ala Asp Lys Ala Val Ser Met Ala
305                 310                 315                 320

Lys Ala Gly Cys Glu Tyr Ile Ser Val Leu Gly Val Asp Phe Met Ser
                325                 330                 335

Glu Asn Val Arg Ala Ile Leu Asp Leu Ala Gly Phe Pro Glu Val Gly
            340                 345                 350

Val Tyr Arg Met Ser Asp Glu Arg Ile Gly Cys Ser Leu Ala Asp Ala
            355                 360                 365

Ala Ala Ser Pro Ala Tyr Leu Asp Tyr Leu Lys Thr Ala Ser Thr Ser
            370                 375                 380

Ser Pro Ser Leu His Val Val Tyr Ile Asn Thr Ser Leu Glu Thr Lys
385                 390                 395                 400

Ala Tyr Ser His Glu Leu Val Pro Thr Ile Thr Cys Thr Ser Ser Asn
                405                 410                 415

Val Val Gln Thr Ile Leu Gln Ala Phe Ala Glu Val Pro Asp Leu Glu
            420                 425                 430

Val Leu Tyr Gly Pro Asp Thr Tyr Met Gly Ser Asn Ile Ala Glu Leu
            435                 440                 445

Phe Thr Gln Met Ser Thr Met Thr Asp Glu Glu Ile Ser Ala Ile His
            450                 455                 460

Pro Leu His Asn Arg Ile Ser Ile Lys Ser Leu Leu Pro Arg Leu His
465                 470                 475                 480

Tyr Phe Gln Asp Gly Thr Cys Ile Val His His Leu Phe Gly His Glu
```

```
                485                 490                 495
Val Val Glu Lys Ile Asn Glu Met Tyr Gly Asp Ala Phe Leu Thr Ala
            500                 505                 510

His Phe Glu Val Pro Gly Glu Met Phe Ser Leu Ala Met Glu Ala Lys
            515                 520                 525

Lys Arg Gly Met Gly Val Val Gly Ser Thr Ser Asn Ile Leu Asp Phe
            530                 535                 540

Ile Lys Glu Arg Val Glu Glu Ser Leu Asn Arg Asn Val Asp Glu His
545                 550                 555                 560

Leu Gln Phe Val Leu Gly Thr Glu Ser Gly Met Ile Thr Ala Ile Val
                565                 570                 575

Ala Ala Val Gly Lys Leu Leu Gly Ser Ala Asp Ser Ser Gly Gly
            580                 585                 590

Ala Lys Val Ser Val Glu Ile Val Phe Pro Val Ser Ser Glu Ser Val
            595                 600                 605

Thr Arg Thr Ser Thr Gly Ser Pro Leu Asp Gln Asn Lys Val Asn Ile
            610                 615                 620

Ile Pro Gly Val Ala Ser Gly Glu Gly Cys Ser Leu His Gly Gly Cys
625                 630                 635                 640

Ala Ser Cys Pro Tyr Met Lys Met Asn Ser Leu Ser Ser Leu Leu Lys
                645                 650                 655

Val Cys Gln Ser Leu Pro His Gly Lys Ala Glu Leu Ser Ala Tyr Glu
            660                 665                 670

Ala Gly Arg Phe Ser Leu Arg Thr Pro Lys Gly Lys Gln Ile Ala Asp
            675                 680                 685

Val Gly Cys Glu Pro Val Leu His Met Arg His Phe Gln Ala Thr Lys
            690                 695                 700

Arg Leu Pro Glu Gln Leu Ile Asn Gln Ile Leu Gln Arg Ser Ser Ser
705                 710                 715                 720

Ala

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
agtggcggag gtaggaattt                                          20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
taagagtgag gtagccggga                                          20

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 11
```

```
cccctttgcca ctttacaaga a                                            21

<210> SEQ ID NO 12
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 12
ttgtgcaaat aggataacaa ctacttt                                       27

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
agctccattt gtacttccgc                                               20

<210> SEQ ID NO 14
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 14
ttctaacaga cgttccaaga tga                                           23

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
cacaagaccc ttcttggtgc                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
acgtggagtg gagaaaccag                                               20

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 17
cagagattac acccattgtg ct                                            22

<210> SEQ ID NO 18
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 18
ccgccgtcaa tgtaggtagt                                              20

<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 19
tgtctcaact tcttgtcaat tgct                                         24

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 20
ccttattatg tcatcctgcg a                                            21

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21
atctttgctt cctcgactcc a                                            21

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
agttaagcgg agcttgatcg t                                            21

<210> SEQ ID NO 23
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 23
atgaggtgct ggcgttga                                                18

<210> SEQ ID NO 24
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 24
ttcagcgtag ctgccttg                                                18
```

<210> SEQ ID NO 25
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 25
ggagtttatc ggatgtcg                                                 18

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
tgtgcagtaa ggaatgcatc                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
gttgtgagcc ggttctgcac                                               20

<210> SEQ ID NO 28
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 28
atggacgccg caaatttagt catga                                         25

<210> SEQ ID NO 29
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 29
agtgactcgg aaataactaa agggtttt                                      28

<210> SEQ ID NO 30
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 30
aagtattagt cacaacatgc agagatgag                                     29

<210> SEQ ID NO 31
<211> LENGTH: 27
<212> TYPE: DNA
<213> ORGANISM: Artificial Sequence
<220> FEATURE:

-continued

<223> OTHER INFORMATION: synthetic oligonucleotide

<400> SEQUENCE: 31
gagctctttc catctctagt aatcaca                                              27

<210> SEQ ID NO 32
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 32
atgtaggtat caggaccata caacact                                              27

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
gttcgaggta aacctacta g                                                     21

<210> SEQ ID NO 34
<211> LENGTH: 41
<212> TYPE: PRT
<213> ORGANISM: Nicotiana tabacum

<400> SEQUENCE: 34

Gly Thr Cys Ile Val His His Leu Phe Gly His Glu Val Val Glu Asn
1               5                   10                  15

Ile Asn Glu Met Tyr Gly Asp Ala Phe Leu Thr Ala His Phe Glu Val
            20                  25                  30

Pro Gly Glu Met Phe Ser Leu Ala Met
        35                  40

<210> SEQ ID NO 35
<211> LENGTH: 41
<212> TYPE: PRT
<213> ORGANISM: Nicotiana tabacum

<400> SEQUENCE: 35

Gly Thr Tyr Ile Val His His Leu Phe Gly His Glu Val Val Glu Asn
1               5                   10                  15

Ile Asn Glu Met Tyr Gly Asp Ala Phe Leu Thr Ala His Phe Glu Val
            20                  25                  30

Pro Gly Glu Met Phe Ser Leu Ala Met
        35                  40

<210> SEQ ID NO 36
<211> LENGTH: 41
<212> TYPE: PRT
<213> ORGANISM: Nicotiana tabacum

<400> SEQUENCE: 36

Gly Thr Cys Ile Val His His Leu Phe Gly His Glu Val Val Glu Asn
1               5                   10                  15

Ile Asn Glu Met Tyr Gly Asp Ala Phe Leu Thr Ala His Phe Glu Ile
            20                  25                  30

Pro Gly Glu Met Phe Ser Leu Ala Met

<210> SEQ ID NO 37
<211> LENGTH: 41
<212> TYPE: PRT
<213> ORGANISM: Nicotiana tabacum

<400> SEQUENCE: 37

Gly Thr Cys Ile Val His His Ile Phe Gly Gly Glu Val Thr Glu Leu
1               5                   10                  15

Val Ala Ala Gly Tyr Gly Asp Ala Tyr Leu Ala Ala His Phe Glu Val
                20                  25                  30

Pro Gly Glu Met Phe Arg Leu Ala Met
            35                  40

<210> SEQ ID NO 38
<211> LENGTH: 41
<212> TYPE: PRT
<213> ORGANISM: Nicotiana tabacum

<400> SEQUENCE: 38

Gly Thr Cys Ile Val His His Ile Phe Gly Gly Glu Val Thr Glu Leu
1               5                   10                  15

Val Ala Ala Gly Tyr Gly Asp Ala Tyr Leu Ala Ala His Phe Glu Val
                20                  25                  30

Pro Gly Glu Met Phe Arg Leu Ala Met
            35                  40

<210> SEQ ID NO 39
<211> LENGTH: 41
<212> TYPE: PRT
<213> ORGANISM: Nicotiana tabacum

<400> SEQUENCE: 39

Gly Asn Cys Ile Val His His Met Phe Gly Asp Asp Val Val Glu Arg
1               5                   10                  15

Val Arg Ser Asn His Ala Asp Ala Phe His Thr Ala His Leu Glu Val
                20                  25                  30

Pro Gly Glu Met Phe Arg Leu Ala Met
            35                  40

<210> SEQ ID NO 40
<211> LENGTH: 41
<212> TYPE: PRT
<213> ORGANISM: Nicotiana tabacum

<400> SEQUENCE: 40

Gly Thr Cys Ile Val His His Leu Phe Gly His Glu Val Val Glu Arg
1               5                   10                  15

Thr Lys Tyr Met Tyr Cys Asp Ala Phe Ile Thr Ala His Leu Glu Val
                20                  25                  30

Pro Gly Glu Met Phe Ser Leu Ala Met
            35                  40

<210> SEQ ID NO 41
<211> LENGTH: 41
<212> TYPE: PRT
<213> ORGANISM: Nicotiana tabacum

<400> SEQUENCE: 41

Gly Thr Cys Ile Val His His Leu Phe Gly His Glu Val Val Glu Lys

```
                1               5                  10                 15
Thr Asn Glu Met Tyr Cys Asp Ala Phe Ile Thr Ala His Leu Glu Val
                20                  25                 30

Pro Gly Glu Met Phe Ser Leu Ala Met
            35                  40
```

<210> SEQ ID NO 42
<211> LENGTH: 41
<212> TYPE: PRT
<213> ORGANISM: Nicotiana tabacum

<400> SEQUENCE: 42

```
Gly Ser Cys Ile Val His Asp Met Phe Gly His Asp Val Val Ser Arg
1               5                   10                  15

Val Arg Glu Gly Tyr Gly Asp Ala Tyr Leu Thr Ala His Phe Glu Val
                20                  25                  30

Pro Gly Glu Met Phe Thr Leu Ala Met
            35                  40
```

<210> SEQ ID NO 43
<211> LENGTH: 41
<212> TYPE: PRT
<213> ORGANISM: Nicotiana tabacum

<400> SEQUENCE: 43

```
Gly Ser Cys Ile Val His Asp Met Phe Gly His Asp Val Val Ser Arg
1               5                   10                  15

Val Arg Glu Gly Tyr Gly Asp Ala Tyr Leu Thr Ala His Phe Glu Val
                20                  25                  30

Pro Gly Glu Met Phe Thr Leu Ala Met
            35                  40
```

<210> SEQ ID NO 44
<211> LENGTH: 41
<212> TYPE: PRT
<213> ORGANISM: Nicotiana tabacum

<400> SEQUENCE: 44

```
Gly Thr Cys Ile Val His His Ile Phe Gly Gly Glu Val Ala Glu Leu
1               5                   10                  15

Val Arg Arg Ala Tyr Gly Asp Ala Tyr Leu Ala Ala His Phe Glu Val
                20                  25                  30

Pro Gly Glu Met Phe Gly Leu Ala Met
            35                  40
```

<210> SEQ ID NO 45
<211> LENGTH: 30
<212> TYPE: DNA
<213> ORGANISM: Nicotiana tabacum

<400> SEQUENCE: 45
aggatgggac atatattgtt catcacctct                                    30

<210> SEQ ID NO 46
<211> LENGTH: 9
<212> TYPE: PRT
<213> ORGANISM: Nicotiana tabacum

<400> SEQUENCE: 46

```
Asp Gly Thr Tyr Ile Val His His Leu
1               5
```

```
<210> SEQ ID NO 47
<211> LENGTH: 30
<212> TYPE: DNA
<213> ORGANISM: Nicotiana tabacum

<400> SEQUENCE: 47
aggatgggac atgtattgtt catcacctct                                    30

<210> SEQ ID NO 48
<211> LENGTH: 9
<212> TYPE: PRT
<213> ORGANISM: Nicotiana tabacum

<400> SEQUENCE: 48

Asp Gly Thr Cys Ile Val His His Leu
1               5

<210> SEQ ID NO 49
<211> LENGTH: 30
<212> TYPE: DNA
<213> ORGANISM: Nicotiana tabacum

<400> SEQUENCE: 49
aggatgggac atgtattgtt catcacctct                                    30

<210> SEQ ID NO 50
<211> LENGTH: 9
<212> TYPE: PRT
<213> ORGANISM: Nicotiana tabacum

<400> SEQUENCE: 50

Asp Gly Thr Cys Ile Val His His Leu
1               5

<210> SEQ ID NO 51
<211> LENGTH: 26
<212> TYPE: DNA
<213> ORGANISM: Nicotiana tabacum

<400> SEQUENCE: 51
cacactttga agttcctggt gaaatg                                        26

<210> SEQ ID NO 52
<211> LENGTH: 8
<212> TYPE: PRT
<213> ORGANISM: Nicotiana tabacum

<400> SEQUENCE: 52

His Phe Glu Val Pro Gly Glu Met
1               5

<210> SEQ ID NO 53
<211> LENGTH: 26
<212> TYPE: DNA
<213> ORGANISM: Nicotiana tabacum

<400> SEQUENCE: 53
cacactttga aattcctggt gaaatg                                        26

<210> SEQ ID NO 54
<211> LENGTH: 8
<212> TYPE: PRT
<213> ORGANISM: Nicotiana tabacum
```

```
<400> SEQUENCE: 54

His Phe Glu Ile Pro Gly Glu Met
1               5

<210> SEQ ID NO 55
<211> LENGTH: 26
<212> TYPE: DNA
<213> ORGANISM: Nicotiana tabacum

<400> SEQUENCE: 55
cacactttga aattcctggt gaaatg                                          26

<210> SEQ ID NO 56
<211> LENGTH: 8
<212> TYPE: PRT
<213> ORGANISM: Nicotiana tabacum

<400> SEQUENCE: 56

His Phe Glu Val Pro Gly Glu Met
1               5
```